United States Patent
Saadat

(10) Patent No.: US 11,850,411 B2
(45) Date of Patent: Dec. 26, 2023

(54) BLADE TYPE CHECK VALVE

(71) Applicant: Mohammad Mohsen Saadat, Soest (DE)

(72) Inventor: Mohammad Mohsen Saadat, Soest (DE)

( * ) Notice: Subject to any disclaimer, the term of this patent is extended or adjusted under 35 U.S.C. 154(b) by 0 days.

(21) Appl. No.: 16/965,592

(22) PCT Filed: Jan. 28, 2020

(86) PCT No.: PCT/EP2020/052023
§ 371 (c)(1),
(2) Date: Nov. 28, 2022

(87) PCT Pub. No.: WO2020/157054
PCT Pub. Date: Aug. 6, 2020

(65) Prior Publication Data
US 2021/0372537 A1    Dec. 2, 2021

(30) Foreign Application Priority Data

Jan. 28, 2019   (DE) .................. 10 2019 000 611.9

(51) Int. Cl.
*F16K 15/14*   (2006.01)
*F16K 27/00*   (2006.01)
(Continued)

(52) U.S. Cl.
CPC ........ *A61M 60/148* (2021.01); *A61M 60/196* (2021.01); *A61M 60/258* (2021.01);
(Continued)

(58) Field of Classification Search
CPC ...... F16K 15/035; F16K 15/144; F16K 15/03; F16K 15/1401; F16K 15/1402;
(Continued)

(56) References Cited

U.S. PATENT DOCUMENTS

| | | | |
|---|---|---|---|
| 3,148,696 A * | 9/1964 | Hoke | F16L 41/045 137/847 |
| RE27,399 E * | 6/1972 | Urso | F16K 15/147 137/516.25 |

(Continued)

FOREIGN PATENT DOCUMENTS

| | | |
|---|---|---|
| DE | 29 49 469 B1 | 5/1981 |
| DE | 2949469 B1 | 5/1981 |

(Continued)

OTHER PUBLICATIONS

Gremium setzt enge Grenzen für neue Herz-OP. In: Spiegel online, Jan. 23, 2015, 1-3, English translation attached.

*Primary Examiner* — Jessica Cahill
(74) *Attorney, Agent, or Firm* — BROWDY AND NEIMARK, P.L.L.C.

(57) ABSTRACT

The invention relates to a blade-type check valve for gaseous and liquid media, to be used in medical technologies as well as in waste water technology with at least three triangular blades, grouped in round configuration at the edges of a polygonal bore of a valve ring or housing, with the number of blades corresponding to the number of faces of the bore. At least at one of the three sides, the valve blades feature an integrated joint, which may also consist of fabric, whereas the two other sides of the valve blades form an articulated lock. The valve can be installed in any position and closes automatically, actuated by the backflow respectively return flow of the medium, without external energy.

13 Claims, 12 Drawing Sheets

(51) Int. Cl.
*A61M 60/148* (2021.01)
*A61M 60/258* (2021.01)
*A61M 60/405* (2021.01)
*A61M 60/892* (2021.01)
*F16K 15/03* (2006.01)
*A61M 60/427* (2021.01)
*A61M 60/268* (2021.01)
*A61M 60/196* (2021.01)
*A61M 60/894* (2021.01)
*A61M 60/585* (2021.01)
*A61M 60/837* (2021.01)

(52) U.S. Cl.
CPC ........ *A61M 60/268* (2021.01); *A61M 60/405* (2021.01); *A61M 60/427* (2021.01); *A61M 60/585* (2021.01); *A61M 60/837* (2021.01); *A61M 60/892* (2021.01); *A61M 60/894* (2021.01); *F16K 15/035* (2013.01); *F16K 15/144* (2013.01); *F16K 27/00* (2013.01); *A61M 2205/04* (2013.01); *A61M 2205/3337* (2013.01); *A61M 2210/125* (2013.01)

(58) Field of Classification Search
CPC ................. F16K 15/1441; F16K 27/00; Y10T 137/7898; Y10T 137/7902; Y10T 137/7885; Y10T 137/7886; Y10T 137/7882; A61M 60/148
See application file for complete search history.

(56) References Cited

U.S. PATENT DOCUMENTS

| | | |
|---|---|---|
| 3,938,197 A | 2/1976 | Milo |
| 4,222,127 A | 9/1980 | Donachy et al. |
| 4,308,805 A * | 1/1982 | Spater ............... F27D 7/04 137/340 |
| 4,308,885 A * | 1/1982 | Geisseler ............ F16K 15/147 220/240 |
| 4,351,358 A * | 9/1982 | Ogle, Jr. ............. F16K 15/035 137/512.1 |
| 4,397,049 A | 8/1983 | Robinson et al. |
| 4,463,248 A | 7/1984 | Katzman et al. |
| 4,465,102 A | 8/1984 | Rupp |
| 4,611,578 A | 9/1986 | Heimes |
| 4,648,385 A | 3/1987 | Oumi et al. |
| 4,731,076 A | 3/1988 | Noon et al. |
| 4,771,925 A * | 9/1988 | Stoffler ............... B05B 11/007 222/207 |
| 4,863,461 A | 9/1989 | Jarvik |
| 5,263,895 A * | 11/1993 | Kraus ................. B60H 1/249 454/162 |
| 5,458,468 A | 10/1995 | Ye et al. |
| 5,503,186 A * | 4/1996 | Orejola ............... B63H 16/04 137/844 |
| 5,628,792 A | 5/1997 | Lentell |
| 5,775,357 A * | 7/1998 | Regna ................. F16K 15/144 137/527.6 |
| 6,035,896 A * | 3/2000 | Liardet ............... F16K 15/144 137/849 |
| 8,141,587 B2 * | 3/2012 | Doig ................... F16K 15/147 137/846 |
| 10,344,882 B2 * | 7/2019 | Skorupa ............. F16K 15/035 |
| 10,487,740 B2 * | 11/2019 | Dehais ............... F02C 9/18 |
| 10,487,955 B2 * | 11/2019 | Czarnecki .......... F16K 15/035 |
| 10,670,158 B2 * | 6/2020 | Wilhelm ............. F16K 27/0209 |
| 10,935,148 B2 * | 3/2021 | Kie .................... F16K 15/035 |
| 10,948,093 B2 * | 3/2021 | Czarnecki .......... F16K 15/035 |
| 2006/0016479 A1 * | 1/2006 | Gonzales ............ E03C 1/104 137/283 |
| 2007/0131285 A1 * | 6/2007 | Zika-Beyerlein ... F02M 26/70 137/512.1 |
| 2015/0308681 A1 | 10/2015 | Martin |
| 2017/0167618 A1 | 6/2017 | Czamecki |
| 2018/0087680 A1 | 3/2018 | Wilhelm et al. |
| 2020/0353141 A1 | 11/2020 | Saadat |

FOREIGN PATENT DOCUMENTS

| | | |
|---|---|---|
| DE | 3316101 C1 | 8/1984 |
| DE | 68906403 T2 | 6/1993 |
| DE | 696 27 510 | 5/2003 |
| DE | 59627510 T2 | 5/2003 |
| DE | 69627510 T2 | 1/2004 |
| DE | 69820603 T2 | 9/2004 |
| DE | 102019000611 A1 | 7/2020 |
| GB | 190926783 A | 9/1910 |
| JP | H025966 A | 5/1983 |
| JP | S6389469 U | 6/1988 |
| JP | 2006346440 A | 12/2006 |
| WO | 2020157054 A1 | 8/2020 |

\* cited by examiner

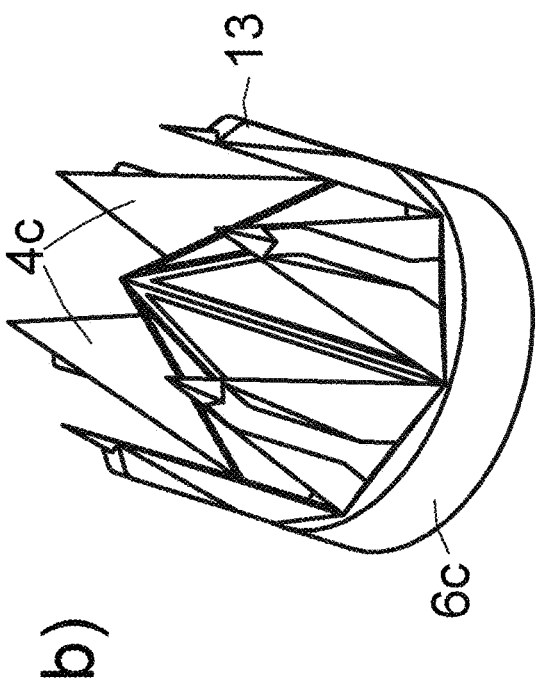
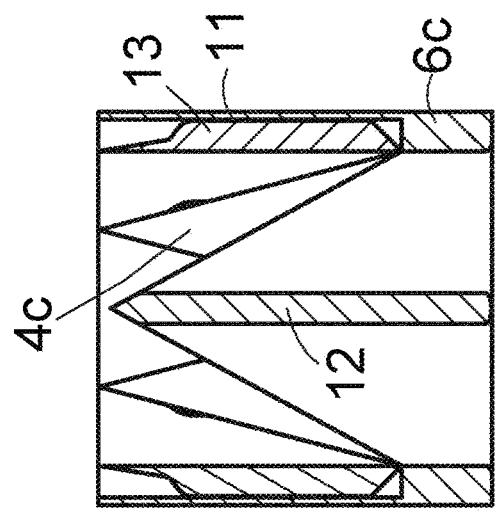
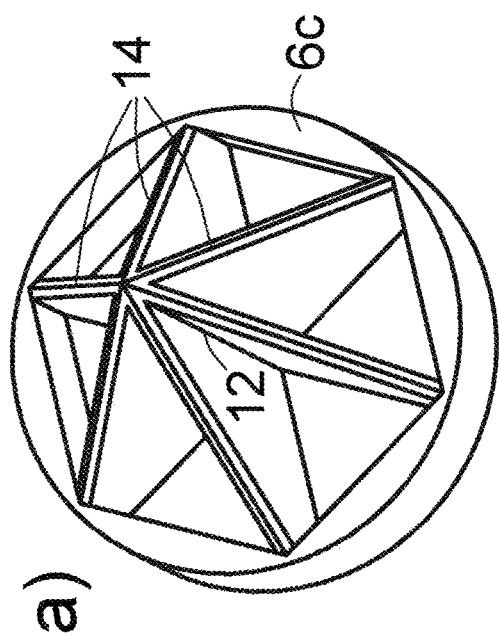
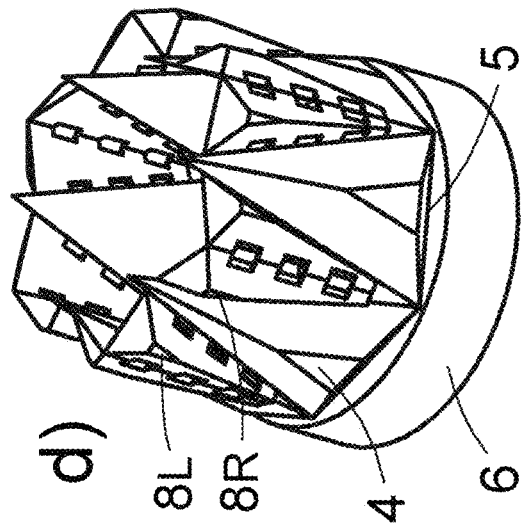
Fig. 6

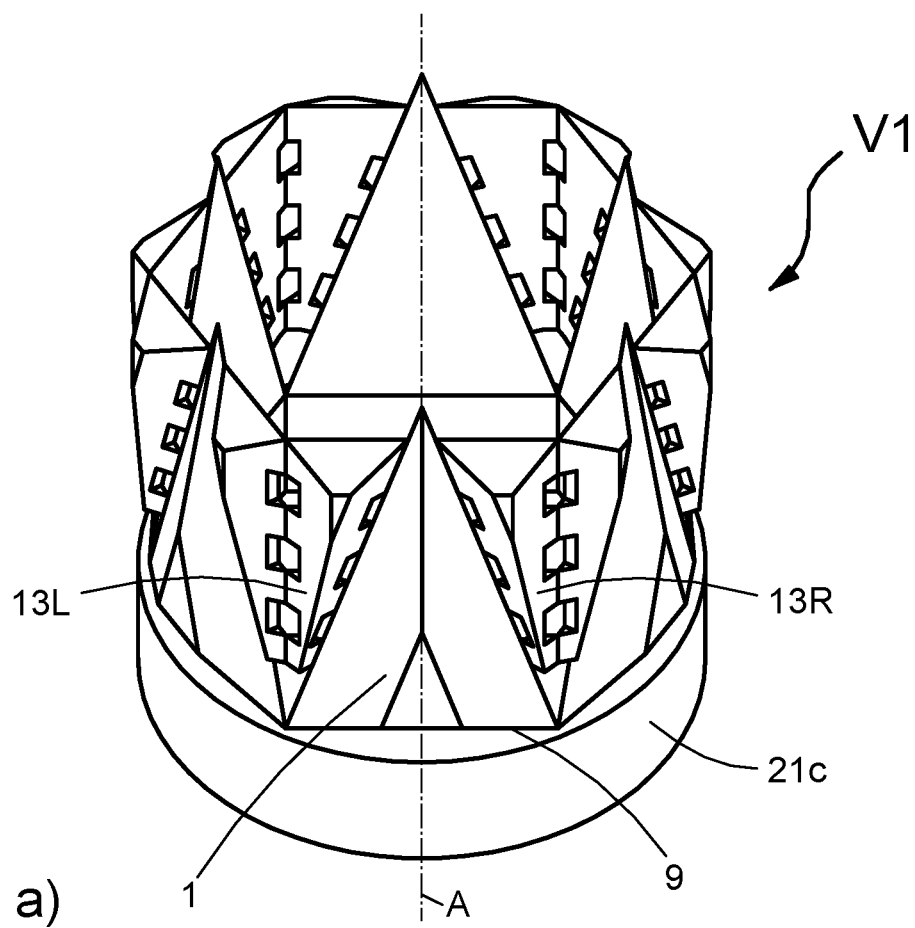
a)
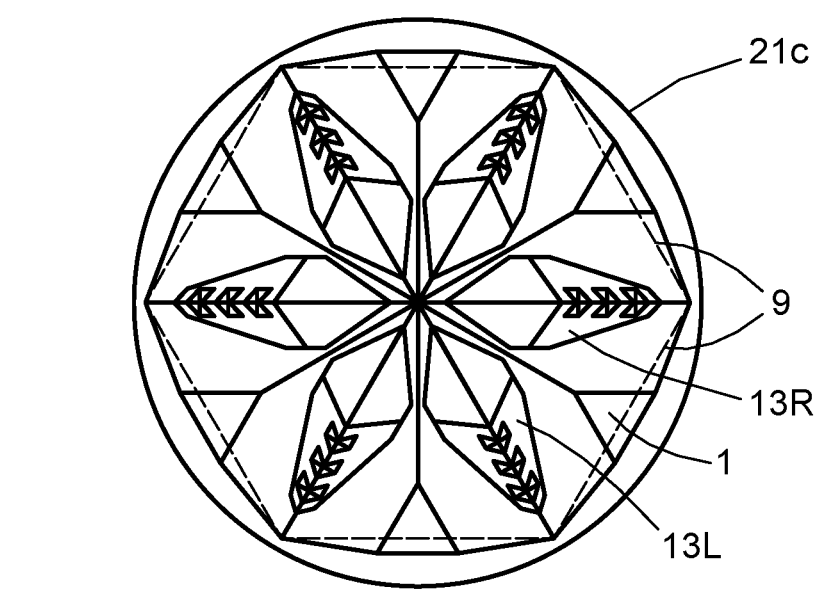
b)
Fig. 8

BLADE TYPE CHECK VALVE

This application is filed under 35 U.S.C. § 371 as the U.S. national phase of International Application No. PCT/EP2020/052023, filed Jan. 28, 2020, which designated the U.S. and claims the benefit of priority to German Patent Application No. DE10 2019 000 611.9 filed Jan. 28, 2019, each of which is hereby incorporated in its entirety including all tables, figures and claims.

The invention described in this document represents a check valve working without an external energy supply and offering a high flow rate, intended for gaseous, liquid up to viscous media, intended particularly for medical applications, e.g. as replacement for heart and venous valves, and to be used also as check valve in the building sector preventing backflow of water or sewage into channels or domestic lines. Numerous blade type check valves with different advantages and drawbacks exist, with respect to flow rate, installation possibilities, admissible material, and last but not least manufacturing cost. Most of these valves feature an eccentric blade entailing turbulences downstream and causing vibrations to itself, accompanied by undesirable noise.

BACKGROUND OF THE INVENTION

DE 29 49 469 B1 describes a lock which in an emergency case is permanently deformed and closes the duct. This lock is based on a folding technique, can be executed only once and is not repeatable. According to the description, this unit represents a folding element, not a valve. A joint is not provided, and none of the movements can be repeated. For tightening, additional protruding sealing elements are required. The folding process cannot be initiated without a considerable pressure difference. Subsequent opening is not possible, so after one single application, the unit must be exchanged.

DE 696 27 510 T2 describes a valve mainly for respirators consisting of several laminas placed around a polygonal frame, attached in an articulated and swiveling manner. These laminas placed side by side in planar configuration, dispose of bending edges running from the outside to the center, with the thickness increasing in this direction. During closure of the valve, they are placed on top of each other, close to the horizontal line, providing for mutual support and sealing. The drawback however is that this is approach is purely theoretical, even not sufficient for light. In practice, available space in the center is too narrow for several overlaps at the same time, as the thickness of material in this position reaches its maximum value. For this reason, the lower edge of the valve blade is not able to withstand the pressure of the streaming medium, and tightness is not ensured. The valve lamellae, called laminas, do not feature any positive lock or synchronization. As a consequence, they do not reach the closed position simultaneously, if not running at the same time and at the same speed. For this reason, overshooting of the closed position cannot be avoided. This principle cannot be considered as safe.

U.S. Pat. No. 3,939,197 describes a valve intended to replace a heart valve, to be inserted into the human heart. It is composed of several lamellae attached to both sides of a ring, by means of two swivel joints each. The closing position of the lamellae is reached by their section which is protruding behind the rotary axis, leaning on the bottom side of the ring. The mechanical function of the valve is not doubted, but the protruding parts of the lamellae as well as hinges and certain portions of the fastening ring interfere with the bloodstream, causing turbulences and increasing the risk of blood clots and thromboses.

U.S. Pat. No. 4,351,358 describes a blade type check valve consisting of a pyramidal case with several trapezoidal through bores, which are opened and closed by means of movable lamellae. These lamellae represent flat trapezoidal elements, installed in swiveling manner and circular configuration around the case, each of them pressed into closing position by means of a torsion spring. Due to the high quantity of torsion springs and swivel joints and the large center space, the available cross section for flow relatively narrow, so this element is deemed to be inappropriate for medical applications like heart or venous valves—also due to the presence of a high number of corners and edges and a turbulent flow. Further drawbacks are abrasion originating from the swivel joints, as well as the limited service life of torsion springs, which in the end will break due to fatigue.

U.S. Pat. No. 4,465,102 describes a blade type check valve consisting of an elastic slotted nipple. Caused by the pressure of the flowing medium, the slots are opened so the medium may pass through. In the opposite direction, the pressure of the medium increases the closing force. In spite of its correct function and good manufacturability, this principle is not adequate for medical applications, as this valve always has to exert a force on its segments for closure; this fact gives rise to turbulences downstream.

U.S. Pat. No. 5,628,792 describes a heart valve composed of three lamellae forming in closed state a circular area. Each of these lamellae is equipped with a swivel joint running on a larger diameter outside the actual cross-sectional area of the valve. This valve is able to work, but not suitable for practical applications. First, the blood passes from a smaller diameter without any transition to a larger diameter which includes a step and accommodates the joints. The resulting Bernoulli effect gives rise to turbulences. Furthermore, the sharp edges of the blade segments in opened state are placed centrally in the bloodstream. Last but not least, in closed state of the valve, the small joints of the individual lamellae are subjected to a significant bending moment originating from the backflow of the blood. For all of these reasons, this valve has yet not been implanted into humans.

US 2017/0167618 A1 describes a heart valve consisting of a multiple configuration of truncated valve lamellae, each of them attached to a circular ring in a pivotable manner by means of a short swivel joint in the zone of the lower circular end. Diagonal webs are attached to the ring as well, radially oriented towards the center of the valve, with the other end being fixed in the center of the profile of the valve by means of a closed disc, thus forming an opened cage acting as a housing.

The movement of the lamellae is synchronized by overlapping of the truncated up to completely conical lamellae, up to the apex.

During rotation of the lamellae around the axis of the swivel joint, each contact point of two adjacent lamellae traverses a different circuit, as the distance to the rotary axis is not identical. For this reason, the lamellae are moving into each other or they separate, but the two surfaces kinematically cannot slide over each other in a homogeneous manner. Furthermore, in opened position, the lower edges of the (circular) lamellae protrude into the stream of the medium. These sharp edges give rise to turbulences and vibration of the lamellae themselves.

As to the conical version of this principle, overlapping of the lamellae is not possible up to the apex, as mutual contact is established before. Only trapezoid versions are realizable, not without a blanking disk in the center of the stream. This disk considerably reduces the flow.

It should also be mentioned that the angle between two adjacent lamellae during rotation of the lamellae around the rotary axis does not remain constant, so their conically designed surfaces perform a reciprocal relative rotational movement. This means that the distance of the two superposed surfaces during movement changes. The resulting volume change entails a pumping effect for the medium flowing in between, slowing down the movement of the valve. Molecules (in the case of liquids) may also be damaged.

The lamellae are intended to close by springs not illustrated in this context, so neither their attachment position nor the limitation of their opening become obvious.

This principle is explained in a too general form with important details and functions missing, furthermore due to the mentioned drawbacks, it is not convenient for medical applications.

SUMMARY OF THE INVENTION

The purpose of this invention consists in the task of developing a valve at a minimum of manufacturing cost, safe, durable, vibration free, working without external energy supply, to be installed in any position and able to achieve a maximum flow rate on the basis of a given volume, giving rise to no or only a minimum of resistance or turbulences.

The invention solves this task by means of the features described in the independent claims.

Dependent claims represent beneficial further developments of the invention. The blade type check valve representing the core of this invention has been designed as a valve automatically opening and closing without external energy, only by means of the current of the gaseous and/or liquid medium. For that purpose, the check valve comprises at least n≥3 triangular-shaped valve blades, accommodated respectively attached by at least one swivel joint each at each side in a pivotable manner and an essentially round configuration, around a polygonal (n corners), preferably hexagonal through bore of a valve ring.

The swivel joint features at least one first and at least one second joint element. According to this invention, at least one element is integrated inside the valve blade.

The fact that at least one joint element is integrated within the corresponding valve blade, means that it is an integral part of the blade, both items being manufactured in one piece in common, and/or mutually connected in an inseparable manner. For production with a fabric joint, integration can be achieved by coating the fabric with a thin layer and then inserting it into the blade.

For fabric joints, it is useful to realize the first and the second joint element preferably in one piece, for instance by means of a piece of fabric. Then one side, the first joint element, is integrated within the blade and the second one is connected to or preferably integrated within the valve ring.

According to the particular type, the check valve comprises at least n≥3 triangular-shaped and particularly three-dimensionally designed valve blades, preferably with a flat surface oriented towards the center axis of the valve and three straight faces limiting this surface.

Preferably at least one of these three faces, is completely or partially as an element of the swivel joint, made of biological or synthetic fibers respectively fabrics or of plastics, preferably directly modeled or integrated within the valve blade. The other two faces are preferably slanting i.e. chamfered in V-form, so that material thickness of the triangular valve blade is maximum in the center of gravity of the triangle, decreasing (becoming thinner) towards the faces and nearly sharp at the edges.

The blades in the simplest configuration are attached in an essentially round configuration, around a polygonal through opening, particularly a bore of a valve ring, at one side by at least one swivel joint, in pivotable manner. The through bore is preferably hexagonal.

The valve ring may dispose of a preferably round or rounded profile. According to the particular design, a polygonal outer profile is also possible. The elements of the swivel joints at the valve ring are preferably realized in the form of a bore or a bolt or by tapering of plastic material as a film joint, preferably at their edges in one piece, so that the edges of the polygonal bore form the rotary axis of the valve blades and a sealing edge. For versions with fabric joints, the section of the fabric joint oriented towards the valve ring, is preferably clamped between the valve ring and a step inside the cylindrical case enveloping the valve. This case for all versions of the valve is used as an optional protection housing.

Preferably at both sides of the joint of the valve blade, respectively at both sides of each valve blade, a left and a right (preferably narrow) lateral blade each is attached in pivotable manner, preferably by means of a biological or synthetic fiber like Nylon, Perlon or silk. At least one right lateral blade and particularly each right lateral blade of the valve blade is connected to the left lateral blade of the right adjacent valve blade in a swiveling manner.

It is particularly preferred that the mutually connected left and right lateral blades or partial blades of adjacent valve blades form a swivel joint each, preferably made of biological or synthetic fiber or silk, with a pivot angle limited to ≤180°, so that during closure of the valve, behind the valve blades, they move from the center axis of the valve in a star-shaped configuration radially towards the outside, then are folded together and placed on top of each other. The length of right and left lateral blades is identical. Their three-dimensional structure has been designed so that their side oriented towards the center axis of the valve is intended to form a level surface. The side representing by its level surface the rotary axis with the valve blade, is chamfered at an angle of approximately 30°. The angle is optimized so that the chamfered sides of the valve blade and the lateral blade are just able to contact each other when the valve is closed. Length and/or angle between the two lateral blades determine position and angular position of the valve blades in maximum opened state.

The joints of the lateral blades are preferably provided only partially and/or within a narrow strip. The complete lateral blades are triangular and mirrored symmetrical, with respect to their surfaces placed on top of each other. The partial blades are sections in any form, cut from the two lateral blades placed on top of each other, with the three joint axes coinciding in any mutual angular orientation, in the point of intersection of the two rotational axes of the valve blades with the valve ring. This means that in this point of intersection, five rotational axes coincide, two of them related to valve blades and the valve ring, and three of them related to the lateral blades with the valve blade and with themselves. This principle ensures a kinematically trouble-free run between open and closed position. In closed state, the configuration proves to be tight and stable.

Another configuration of the valve according to this invention features positive as well as negative elements of a lock, at each side of the valve blade adjacent to the valve ring, so that a positive element during closure of the valve is continuously inserted into the negative element, meanwhile rotating. At the end of the closing process, all valve blades are mutually plugged into each other (at the faces pointing from the center axis radially outwards to the valve ring) in swiveling configuration. With respect to the rotation depending on the quantity of valve blades and their inclination in closed state, this joint requires a corresponding degree of freedom.

This joint lock at the edges of the valve blades exists only partially, from the valve ring up to a point located close to the tip of the valve blade, cylindrically or preferably in conical or truncated shape, with the apex pointing towards the valve tip.

To the lateral face (pointing towards outside) of the hollow joint (negative) element preferably bores or slots in comb-type are provided, so that molecules and important fluid components may traverse without being damaged, and the opening process of the valve blades is not disturbed by suction effects.

The third face of the valve blade is partially modeled as an element, a bolt or a bore, with its second joint element located at the valve ring. This joint can easily be plugged in or replaced by a fabric joint.

In a further configuration, the two chamfered faces of the valve blade adjacent to the valve ring are modeled as elements of a turn-slide V-joint, in kinematics also called knife-edge joint. One face (e.g. the right one) is chamfered in positive V-form like a knife edge, whereas the other one features negative V-joint as a V-slot cut from the valve material, oriented towards the adjacent valve blade. The angle of this negative V-slot exceeds the angle of the positive cut of the other face. The deep tip of the V-slot corresponds to the straight face of the valve blade. In opened state of the valve, these two V-shaped structures (positive and negative) of two adjacent valve blades together form one bent up knife-edge joint—just when their flat faces are oriented approximately vertically to the valve ring—, with a contact point at the intersection of the rotary axes of the two valve blades with the valve ring. During closure of the valve, the positive V-element—starting from the valve ring up to the valve tip—continuously migrates into the negative V-slot, meanwhile rotating from the internal flank which is closer to the valve axis, to the outer flank of the slot. In closed state, the two knife edges are completely placed on each other, tightening the whole configuration by means of their (positive respectively negative) tips. In this position, the valve is kinematically overdetermined several times, therefore each swivel joint between the valve blade and the valve ring disposes of an additional axial degree of freedom. This means that the swivel joint from now on can be regarded as turn-slide cylindrical joint. The axial movement however is very low, just sufficient to compensate production tolerances.

The material representing the negative element (e.g. the V-slot) is preferably modeled cylindrically, conically or pyramidally, stopping at a point close to the tip of the valve blade.

This valve structure ensures maximum stability in every position, especially in closed state. For the valve blades, in closed state no limitation and no additional support by the case or housing is required.

In maximum opened state, the position is limited by a slightly elevated point at the rear side of the valve blade, which is oriented towards outside. This limitation takes place when the mentioned elevated point of the blade reaches the wall of the round case used as protection housing. Contact position is above the valve ring. In opened state, the valve blades are oriented perpendicularly to the ring area, at maximum. The backflow of the flowing medium presses against the slanted chamfers of the two erected valve faces and of the lateral blades, thus automatically closing the valve blades. This action does not depend on the direction of gravitation, since the valve blades are floating in the medium and their own weight can nearly be neglected. Synchronous motion of all valve lamellae is ensured by intertwining of the sides of adjacent valve blades.

For numerous configurations according to this invention, managing without lateral blades and without forced synchronization, an opened pyramidal grid structure is attached to the valve ring, acting as a support for the valve blades in closed state and enhancing tightness of the whole entity. The opening of the valve blades is limited by leaning the bulge-shaped ribs at their rear side on the tube-shaped housing surrounding the entire valve.

For all versions of the blade type check valve basic to this invention, an essentially ring-shaped body as valve case or as a part hereof features in its hollow center a polygonal (n corners) through bore. The number n amounts at least to three; the upper value is limited by the outer diameter of the ring-shaped body and the width of the valve blades. At each edge of a face of the polygonal bore, a valve blade is provided in swiveling manner, also called main blade. The valve blades are triangular-shaped with two legs of equal length, preferably consisting of solid material like metal, plastics or composites.

The third (i.e. generally the shortest face of the valve blades each) is attached in swiveling manner to the edges of the polygonal bore of the hollow ring. The edges preferably form the axis of the swiveling respectively turn-slide cylindrical joints each, as well as a sealing edge.

In order to synchronize the motion of the valve blades, in a first and preferred version of the valve, each valve blade at its right and at its left side is connected by its legs of equal length to one lateral triangular-shaped lateral blade each, in swiveling manner. Each lateral blade is a mirrored image of the other one. These lateral blades consist of solid material as well and usually dispose of three faces of different length. The longest face is connected to the valve blade in swiveling manner, whereas the shortest face represents the outlet of the check valve. The third faces of the two mutually mirrored lateral blades in common form a swivel joint with a rotating angle limited to 180°. During closure of the valve, they are folded together and placed completely on top of each other, oriented from the center axis of the valve in star-shaped configuration radially towards the outside.

The main blades in closed state preferably form a triangular or polygonal (e.g. a hexagonal) pyramid, and in opened state a half pyramid up to a cylindrical or polygonal tube, with n corners at the inlet and 2 n corners at the outlet.

Another useful version of the valve uses only a narrow section of the lateral blades for synchronization of the blades, using springing plastic elements in angular state without springs, with a tendency to automatic closure (therefore ensuring also automatic closure of the valve).

An interesting beneficial version of the valve is characterized by a honeycomb-shaped open and pyramidal grid structure built over the ring of the valve. Open in this context means open with respect to the current, respectively that the grid structure always features at least one open flow area. In closed state, the valve blades are put on the triangular-shaped or polygonal openings of the faces of the pyramidal structure within the valve housing. Towards outside, the opening width of the valve blades is restricted individually by leaning of the reinforcement ribs respectively their rear side on the inner wall of the housing.

The grid structure is composed of honeycomb-shaped thin channels or ribs side by side, with any geometrical shape in the profile, ensuring a low friction flow for the gaseous or liquid medium passing through. The walls and ribs of the grid structure start from the valve ring, in radial and preferably ascending orientation towards the center axis and the tip of the valve, providing for straight or slanted support of the valve blades. These supporting ribs may also be present without honeycomb formation.

All the described versions of the valve open and close automatically without an external energy supply, may be installed in any position and produced by injection molding of plastics or by 3D printing in one piece.

BRIEF DESCRIPTION OF THE DRAWINGS

Figure 1:
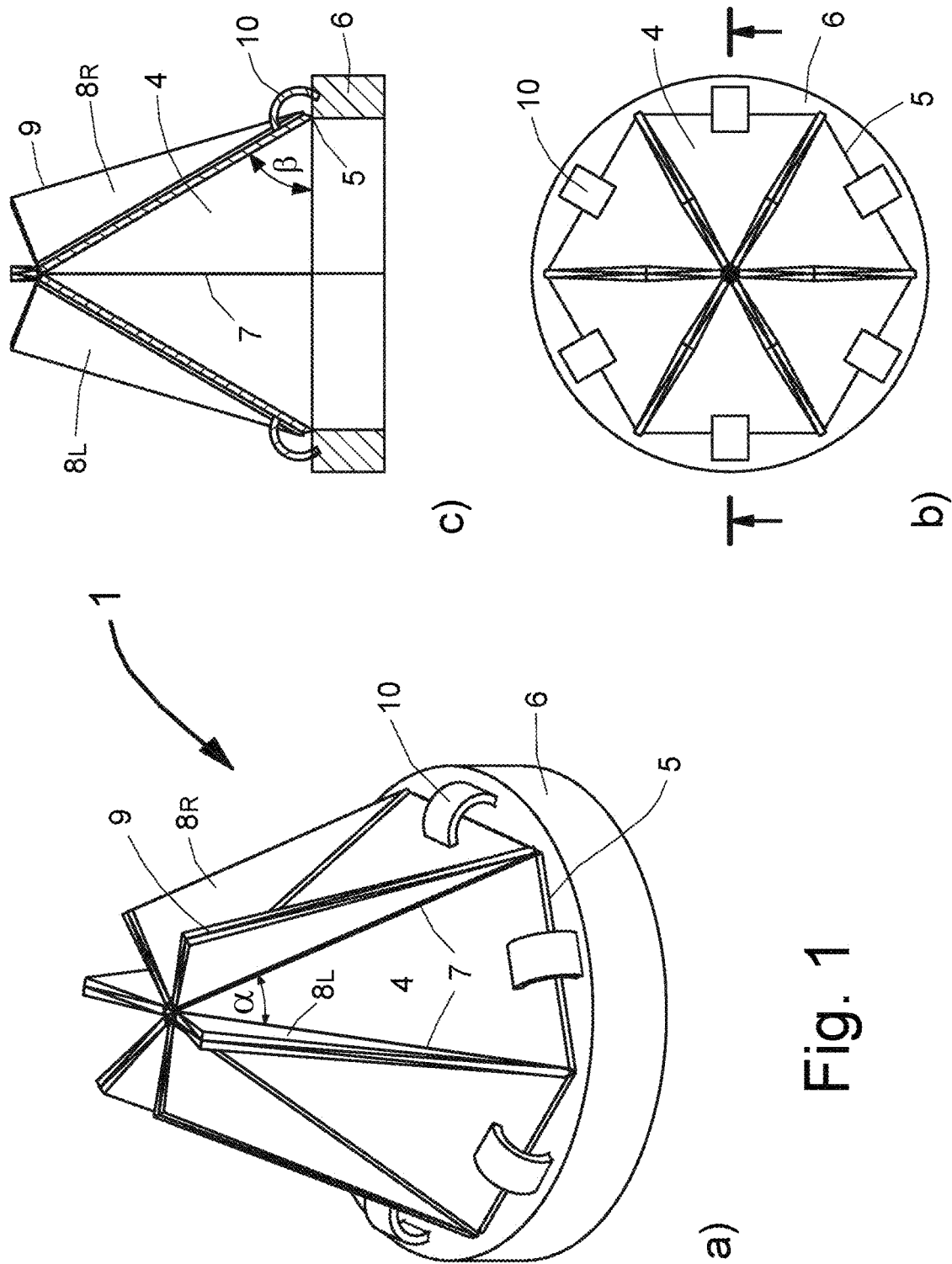

Detailed description of illustrations:

FIG. 1 shows three views (a, b and c) of a triangular valve blade.

Figure 2:
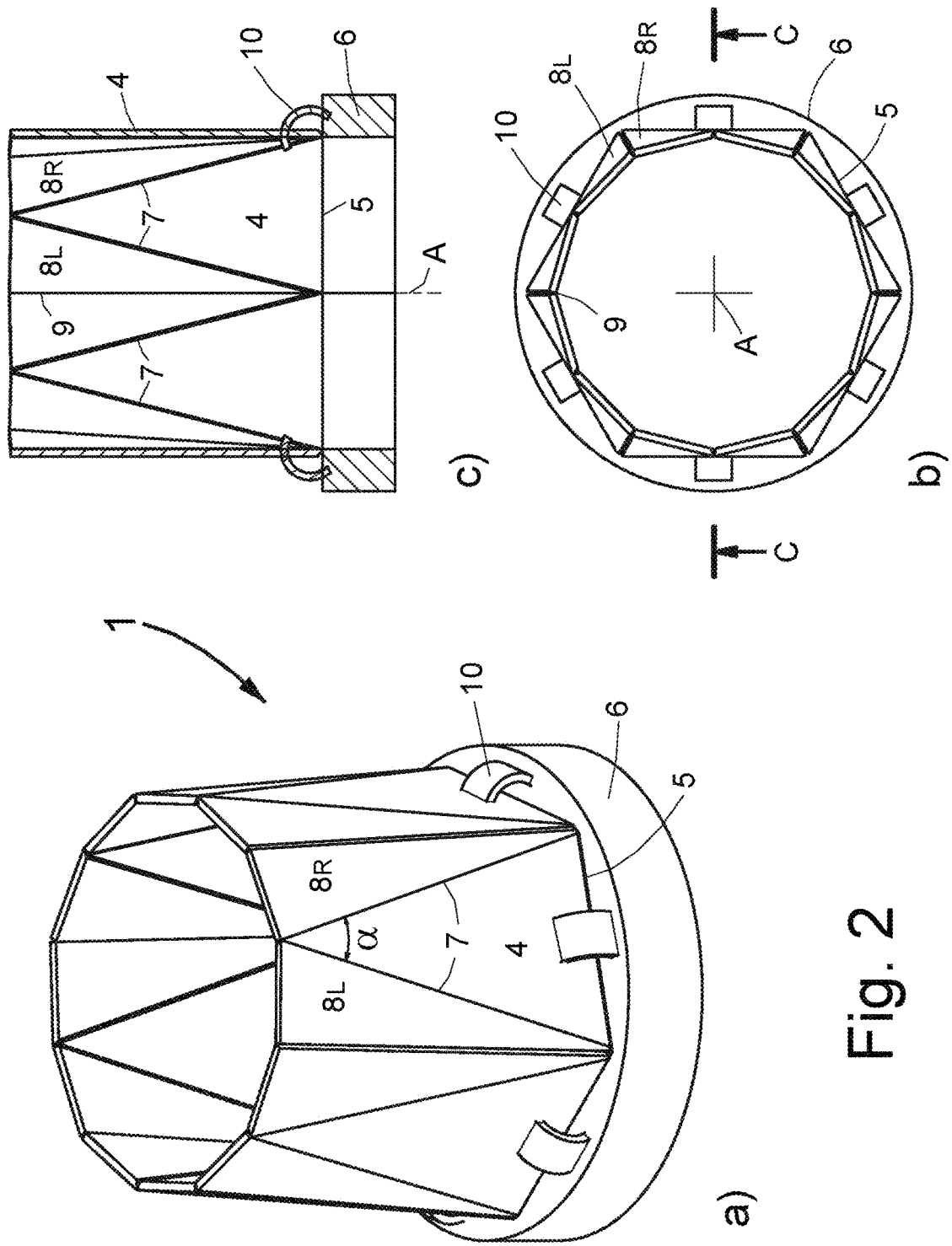

FIG. 2 shows a simple valve blade a) with a fabric joint for attachment to the valve ring b) with a bulge on its back and a fabric joint for attachment to the valve ring, c) additional attachment at both sides by fabric respectively fiber joints to the two short lateral blades, d) a simple valve blade attached at the sides to two lateral blades by only partially provided fabric respectively fiber joints and finally e) six valve blades with two short lateral blades each, attached by means of a woven fiber replacing all joints at the same time, Excessive fabric is removed.

Figure 3:
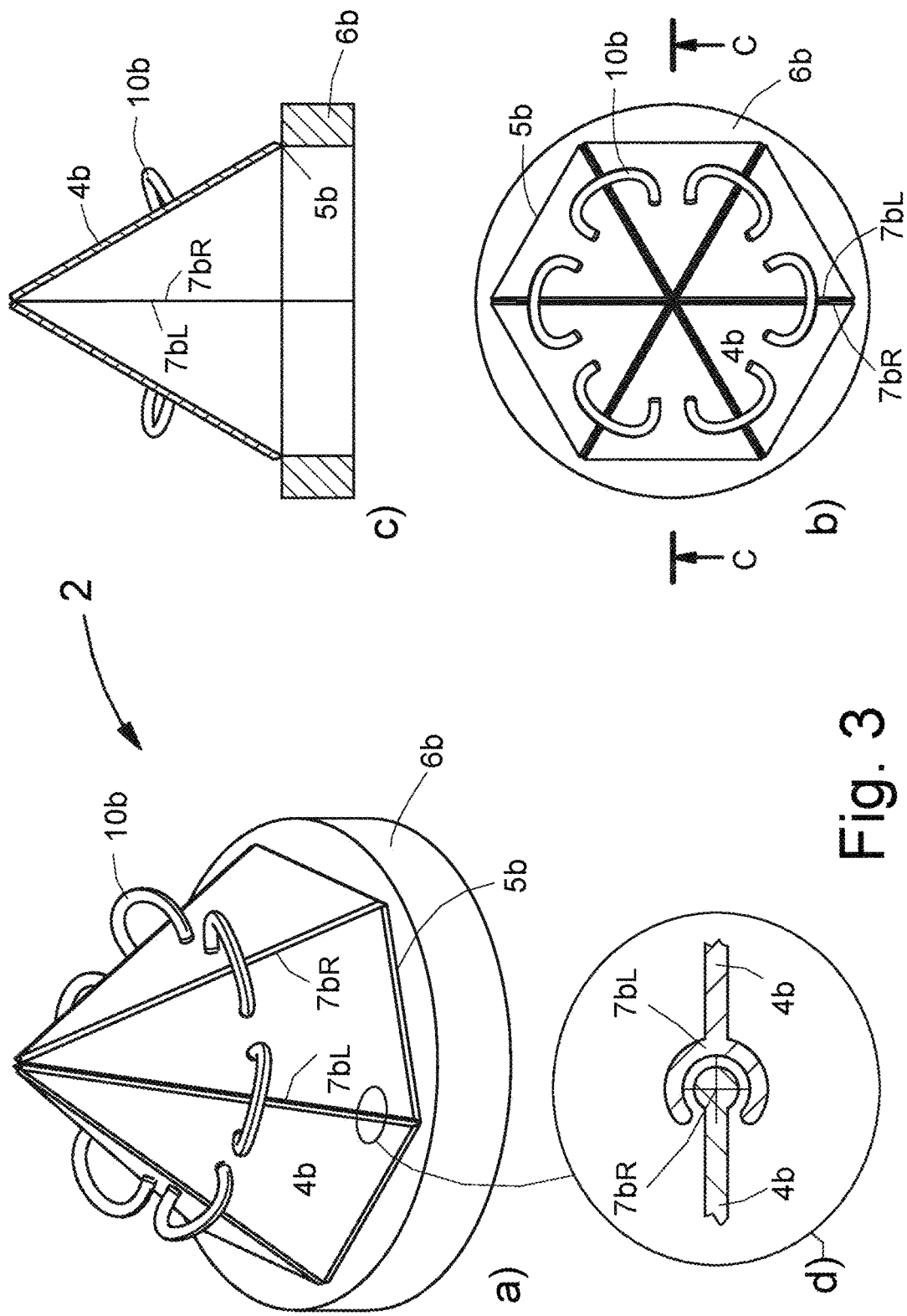

FIG. 3 shows a version of the valve blade with a cylindrical joint at the side which is oriented to the attached valve ring, and a positive as well as a negative cylindrical lock element each at the two other faces of the blade.

Figure 4:
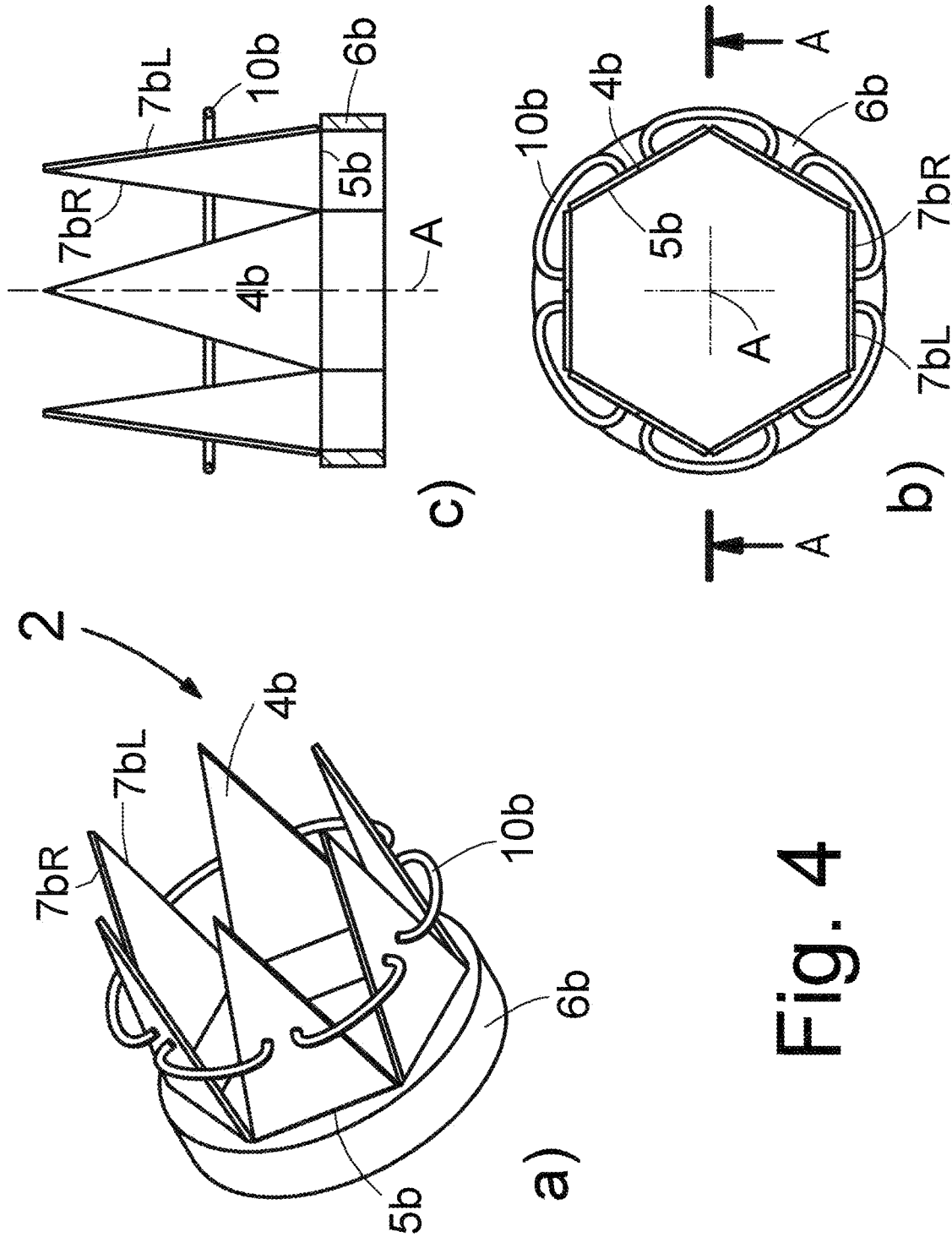

FIG. 4 shows a further version of the valve blade with a cylindrical joint at the side which is oriented to the attached valve ring, and a positive as well as a negative wedge lock element each at the two other faces of the blade. In this case the lock elements are wedge-shaped.

Figure 5:
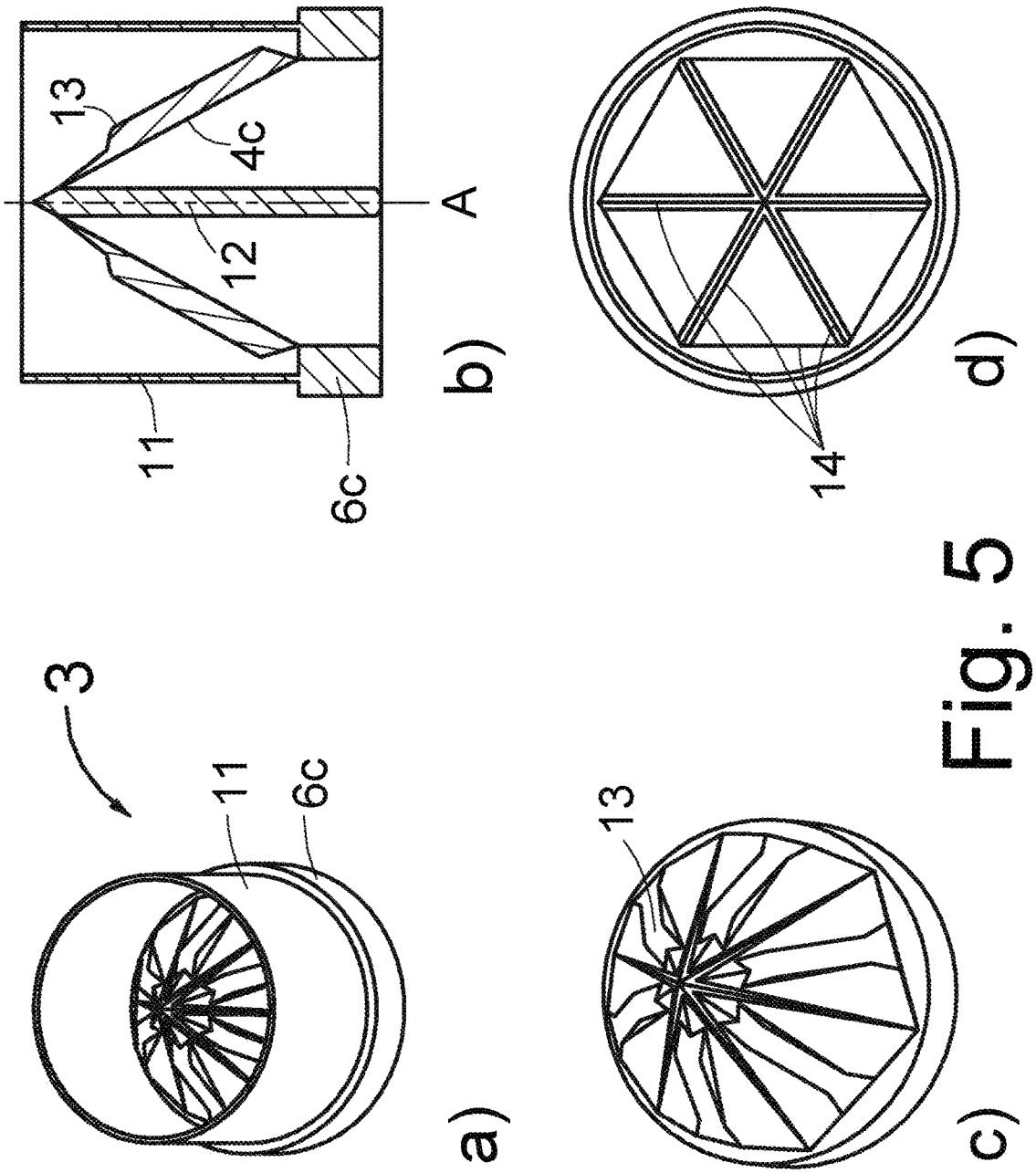
Figure 7:
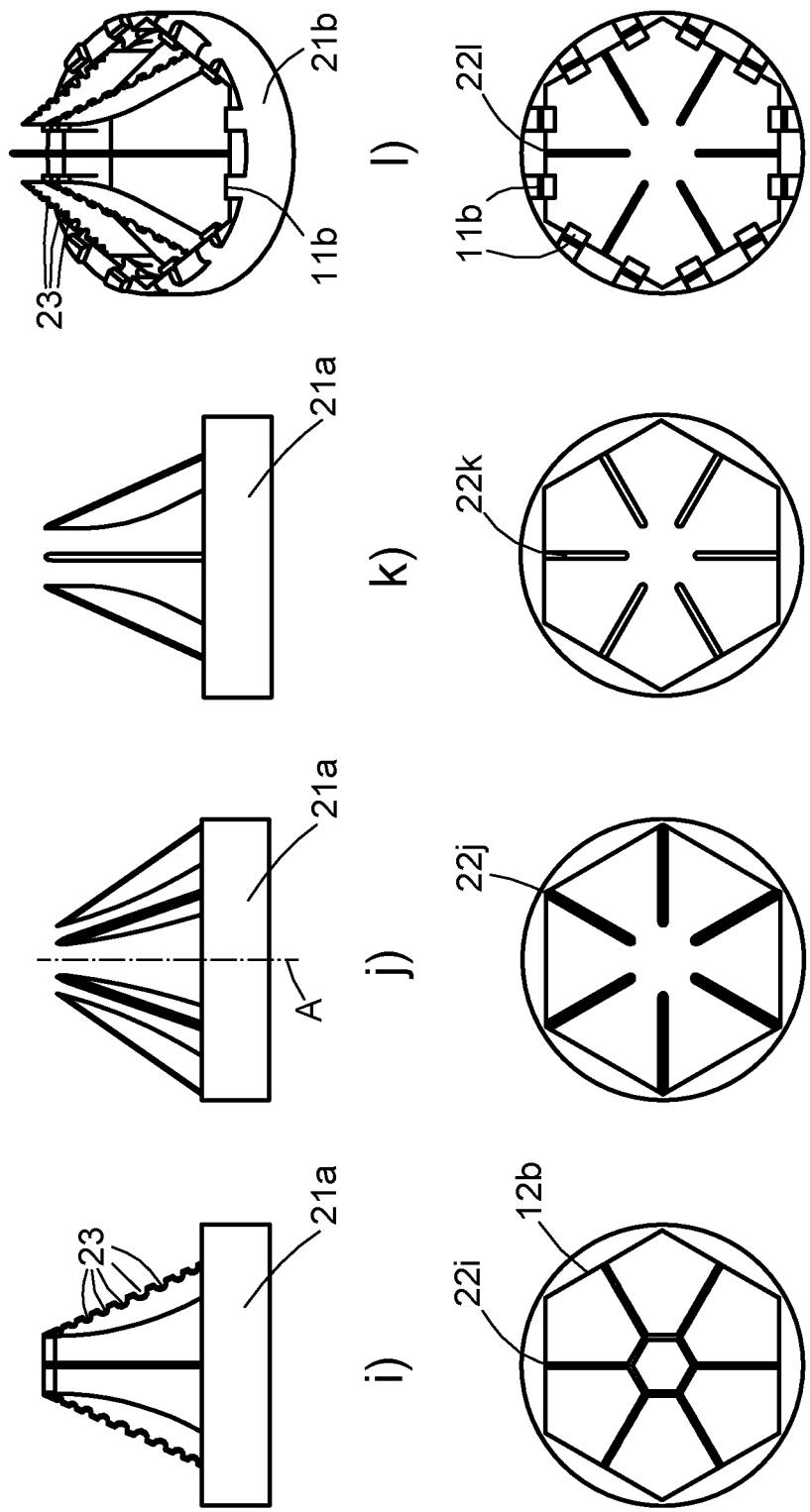

FIGS. 5, 6 and 7 show in two views different versions of the valve ring according to the invention, as a valve housing without valve blades with a pyramidally composed honeycomb-shaped grid structure inside the valve ring.

FIG. 8 shows a valve according to the invention consisting of six valve blades and twelve lateral blades, all of them triangular, representing a three-dimensional mechanism with 24 swivel joints, automatically opening and closing actuated by the flow of a gaseous or liquid medium.

Figure 9:
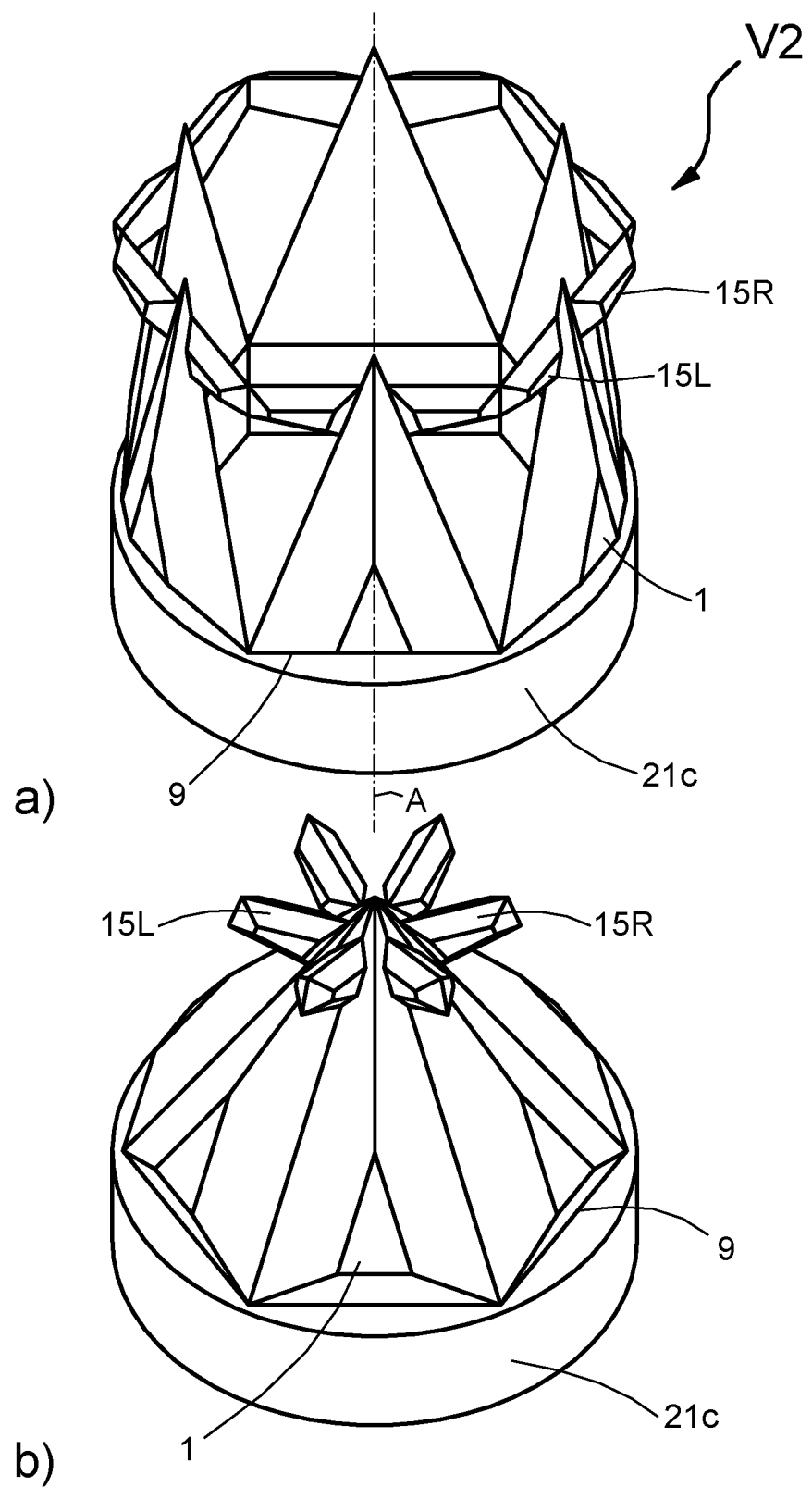

FIG. 9 shows a valve according to the invention similar to the type shown in FIG. 8, but with lateral blades shortened to the minimum. Already during production, the joints of the lateral blades may be subjected to a preload giving rise to the tendency to push the valve blades always in closing direction.

Figure 10:
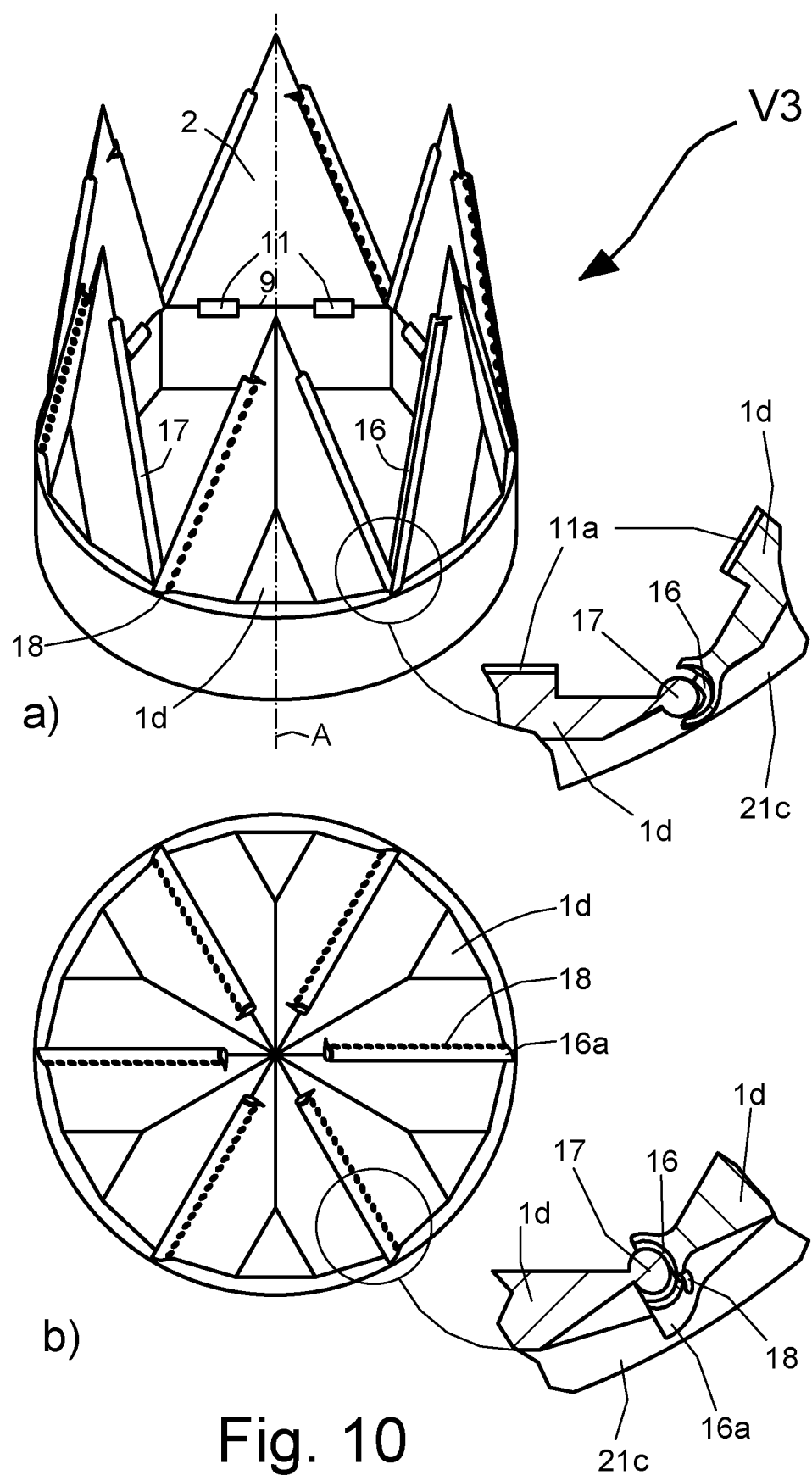

FIG. 10 shows another version of the valve according to the invention. In this configuration, two faces of each valve blade, particularly two face tips of two adjacent valve blades mutually opposed when the valve is in closed state, are positively and negatively shaped like a pressure lock so they able to intertwine like a swivel joint.

Figure 11:
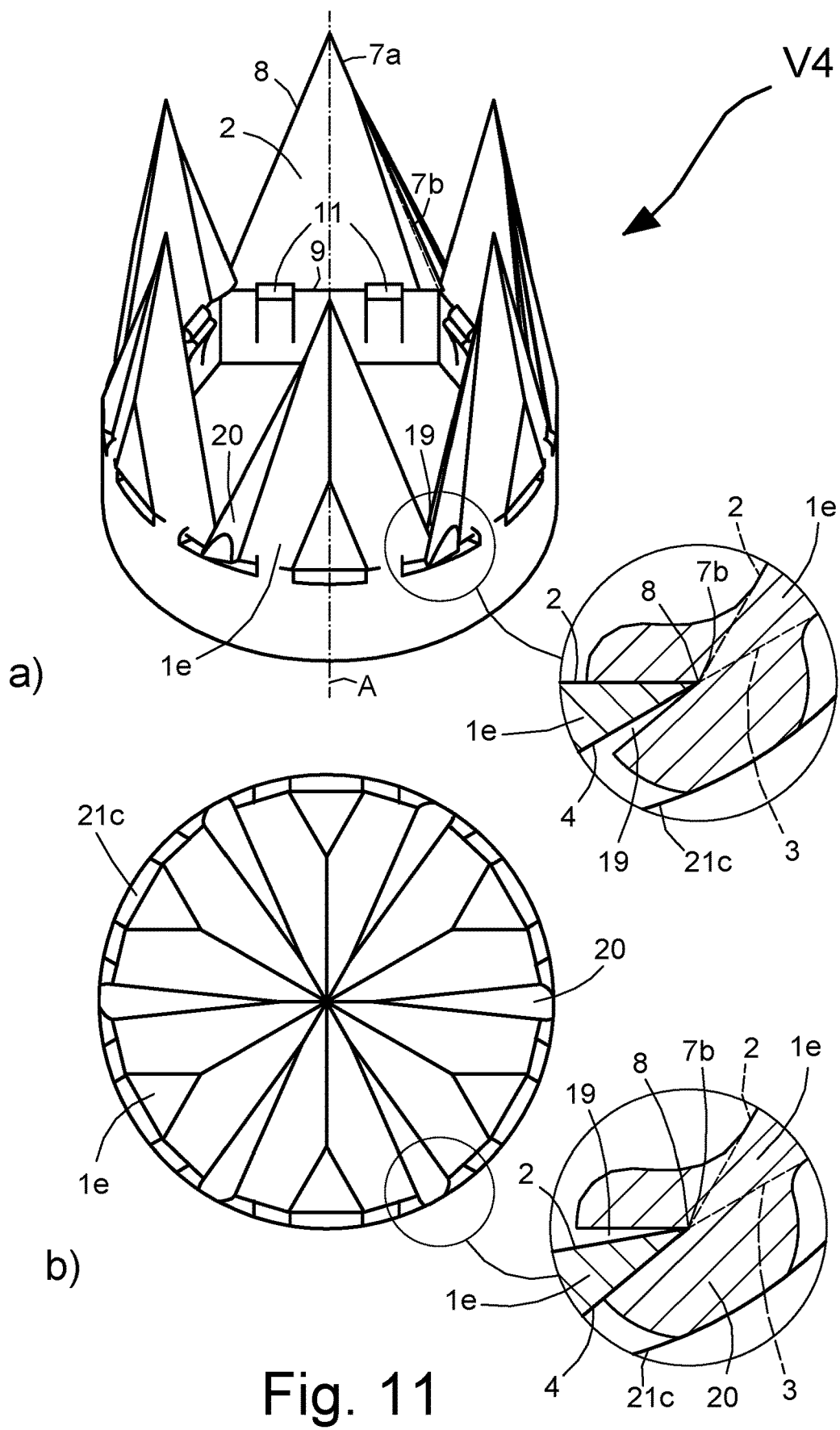

FIG. 11 shows a more advantageous version of the valve according to the invention. In this configuration, two faces of each valve blade, particularly two face tips of two adjacent valve blades mutually opposed when the valve is in closed state, are positively and negatively wedge-shaped so they able to intertwine like a knife-edge joint.

Figure 12:
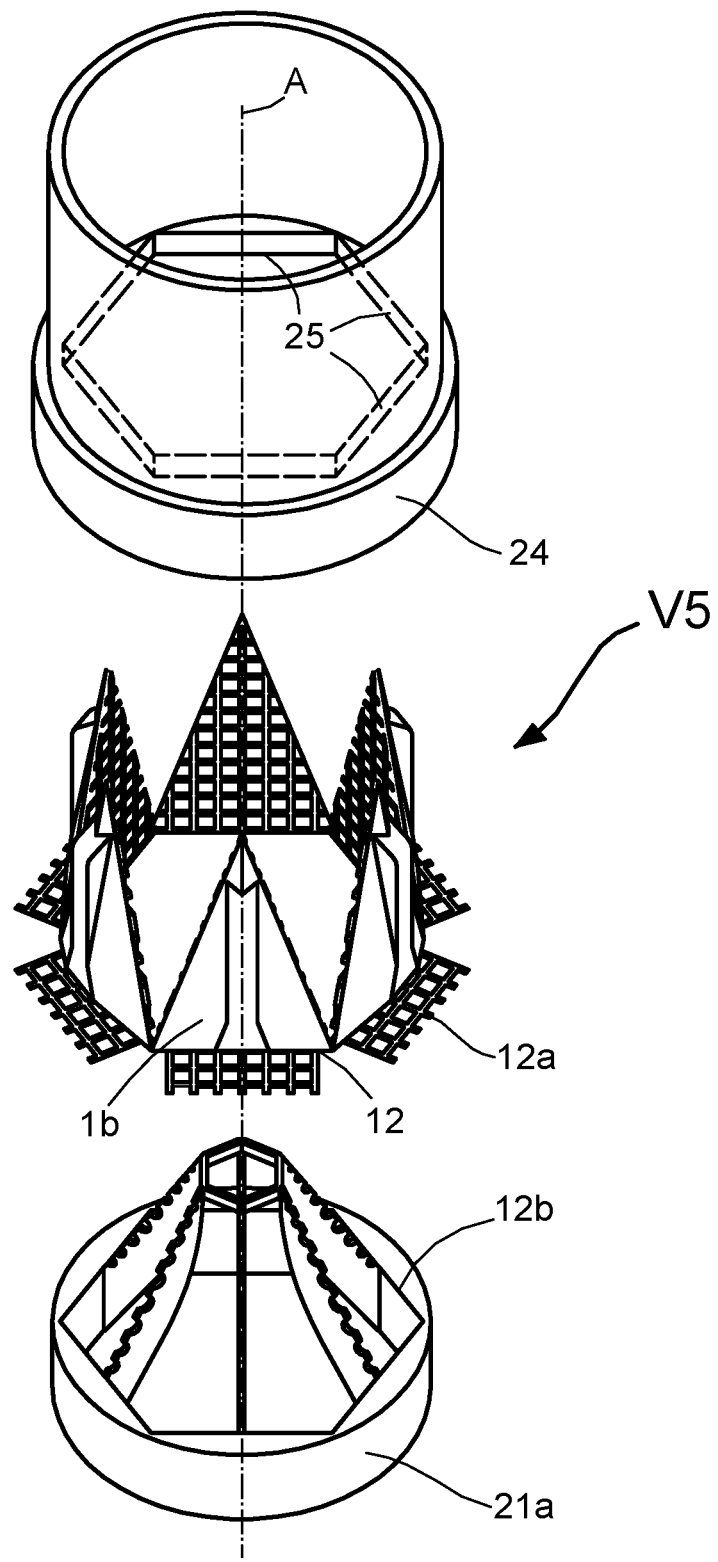

FIG. 12 shows views of the valve according to the invention with fiber fabric joints composed of three parts.

The number of identical parts is always the same. Indices with letters designate different versions or sizes of the same element.

DETAILED DESCRIPTION

FIG. 1 shows three versions of a valve blade of a check valve according to the invention. All valve blades (1) are modeled three-dimensionally with a triangular main area (2) are oriented towards the interior respectively the center axis of the valve. The lateral faces of the valve blades (3, 4 and 5) diagonally rise from the straight edges (7, 8 and 9) of the main area up to the rear side (6) of a half pyramid or to the tip of a pyramid, forming together with the main area three preferably sharp edges (7, 8 and 9), used for tightening and/or formation of joints and locks. Areas (3, 4, 5 and 6) at the rear side of the valve blade act as limitation of the valve opening as well as limitation of the motion of the lateral blades (if provided). The rear side (6) of valve blade (1b) is reinforced along the longitudinal axis. The valve blades (1) consist of solid material like plastics. Joint and seal elements are preferably parts of the valve blades, so they are usually produced together as one single piece. The joints consist of elements in plug-in configuration. A row of burls (10) is provided on the main area (2) of valve blade (1b), useful to minimize the contact area when leaning the valve blades on the honeycomb-shaped grid structure. This enables the valve blades to be opened in shorter time, and furthermore during closure reduces compaction of possibly sensitive molecules e.g. in blood.

The edge (9) of the valve blade shown in FIG. 1c features two first joint elements (11a) of a swiveling joint. Their common rotary axis is in alignment with edge (9). The counter element of the joint is located at the valve ring, so the entire set-up represents a plug-in swivel joint not requiring additional parts.

FIG. 2 shows two valve blade types a) and b) with one joint element each (12a) made of biological or synthetic material like silk, nylon or perlon, either directly inserted by 3D printing into the material of the valve blade during production, or attached afterwards.

In FIG. 2c, the lateral blades (13L and 13R) are not modeled completely. No joint elements (14) are provided at the tips of the triangular main face (2) of the valve blade. The lateral blades as well are attached to the valve blade in swiveling manner by means of fiber material (12a), with the joint elements (14L and 14R) of the lateral blades not being provided completely; they only exist in form of segments.

As shown in FIG. 2d, the lateral segments are reduced to a narrow segment (15L and 15R), in order to reduce the flow resistance further. The narrow segments of the lateral blades (15L and 15R), similarly to the valve blades are laterally chamfered, particularly at the faces mutually opposed and the faces oriented towards the valve blades, at an angle enabling the two edges at the left and at the right side to be used as joint elements, and enabling the upper and lower edge conveniently to be designed according to the flow.

FIG. 3 shows in three views a three-dimensionally designed valve blade (1d) with a main area (2), three diagonally chamfered lateral faces (3, 4 and 5), as well as three straight edges (7, 8 and 9). The edge (9) is partially modeled as an element (11a) of a swiveling joint. The second element of this joint is located at the valve ring. This convenient plug-in joint can also be replaced by a fabric joint, as shown in FIG. 2. The other two edges (7 and 8) of valve blade (1*d*) are preferably subdivided into two sections a (above, close to the valve tip) and b (below, in the vicinity of the valve ring).

Within the short upper zone, the edges (7*a* and 8*a*) of valve blade (1*d*) are chamfered in an acute angle of approximately. 30° and straight. In the lower and much longer zone (7*b* and 8*b*), the edges are virtual. Around these edges, an opened, preferably cylindrical or conical hollow body (16) is modeled at one side (shown in the illustration on the left), and at the other side (shown on the right) another cylindrical or conical entity (17), appropriate to the first body. In closed state of the valve, the two axes (A7 and A8) of these two positively and negatively formed bodies (16 and 17), mutually aligned, represent the virtual edges (7*b* and 8*b*) of the main area (2) of the valve blade. This way, in closed state of the valve, the right edge of a valve blade together with the left edge of the right adjacent valve blade together form a lock.

To the lateral face (16*a*) of the hollow edge (16), which is pointing towards outside, preferably either bores (18) or slots in comb-type are provided, so that molecules and important fluid components may traverse without being damaged, and the opening process of the valve blades is not interfered by suction effects. The edges (7*b* and 8*b*), as shown in FIG. 4), may also be designed with a truncated or tapered shape, positively and negatively. In this case, orientation of the apex towards the valve tip is recommended.

FIG. 4 shows a three-dimensionally designed valve blade (1*e*) with two joint elements (11*a*) of a swiveling joint at the edge (9) of the main area (2), a wedge—respectively V-shaped right edge (8) at an inclination of 30°, and a left edge (7) composed of two sections (7*a* and 7*b*). The short upper section (7*a*) is V-shaped at an inclination of 30°, whereas the longer low section (7*b*) represents the cutting edge of two levels of a hollow V-shaped slot (19). The V-angle of the hollow wedge, respectively the V-shaped slot, preferably exceeds the angle of inclination of edge (8) by approximately 10°. Its opening to the adjacent valve blades is conveniently oriented, so that in opened state of the valve, the internal outside (2) of edge (8) contacts or approaches the inside of the V-slot, whereas in closed state, edge (8) of each valve blade (1*e*) contacts or approaches the edge (7*a* and 7*b*) of the adjacent valve blade, as well as outer surface (4) of edge (8) at the outside of the V-slot. This way a knife-edge joint is formed between the positive wedge of a valve blade and the negative wedge of the adjacent valve blade. The sharp edge of this joint seals both valve blades without any other sealing element.

For swiveling joints (11*a*) in valves with valve blades according to (1*e*), a second degree of translation is added to the degree of freedom of rotation. This additional degree of freedom is provided only in a very narrow zone, as symbolically shown in the illustration. This enables all valve blades to be pressed against each other in circumferential direction, when the valve is closed, simultaneously centered by means of the knife-edge or wedge joints. This feature optimizes the tightness of the configuration.

FIGS. 5, 6 and 7 show two versions (21*a* and 21*b*) of a valve ring (21) with hexagonal through bore. The inner edges of the hexagons act as elements of swiveling joints, improving tightness. These edges are used either as elements of an integrated film joint (21*a*), or a fiber joint (12*b*) or as a part of a swiveling joint (11*b*) manufactured in one single piece at the valve ring (21*b*).

A grid structure (22) with different geometrical shapes (a to l) is located inside the valve ring (21 and 21*b*). This grid structure is mainly composed of thin ribs, radially ascending from the valve ring in direction of the center axis (A) and towards the tip of the valve in a pyramidal arrangement. The grid structure supports the simple valve blades according to FIGS. 1*a*, 1*b*, 1*c* as well as 2*a* and 2*b*.

In a simple form according to FIGS. 5*a* and 5*b*, the radially oriented ribs (22*a* and 22*b*) form honeycomb-shaped opened and angular channels, enabling the stream to pass through in direction of the longitudinal axis of the valve. The honeycomb-shaped grid structures (22*c*, 22*d*, 22*e* and 22*f*) according to FIGS. 5*c*, 5*d*, 6*e* and 6*f* keep the center of the valve clear in order to minimize flow resistance. The lowest resistance is offered by structure (22*e*) according to FIG. 6*e*. Supplementary advantages become possible by the funnel shape of radial ribs (22*g*, 22*h* and 22*i*) shown in FIGS. 6*g*, 6*h*, and 7*i*, able to increase the flow further.

Saw-tooth shaped recesses (23) are provided in the radial ribs (22*i* and 22*l*) shown in FIGS. 7*i* and 7*l*. They reduce the contact area between valve blades and ribs and simultaneously the resistance when the valve blades are just opening. A combination of serrated ribs (22*i* and 22*l*) according to FIGS. 7*i* and 7*l* and a valve blade (1*b*) with burls according to FIG. 1*b*, avoids damages of sensitive molecules inside the flowing medium considerable and prevents the adhesive effect which could arise during the opening procedure.

In FIG. 7*l*, the second joint elements (11*b*) of a plug-in swiveling joint already mounted to the valve ring, are manufactured as one single piece. These elements can also be manufactured as one single piece as a film joint together with the valve blades, ribs and grid structure.

FIG. 8 shows a first valve according to the invention (V1) in two views a) in opened and b) in closed state. The valve consists of a valve ring (21*c*) with hexagonal through bore. To each side of the hexagonal bore, a valve blade (1) at its edge (9) is attached together with its lateral blades (13L and 13R) acc. to FIG. 2*c* only partially provided. Attachment is carried out by means of a film joint or a joint made of fiber material. The lateral blades (13L and 13R) are mutually connected in swiveling configuration as well. The joint between the lateral blades enables them to be completely placed on top of each other on the rear side of the valve and between the valve blades, whenever the valve is closed. In opened state of the valve, between the two lateral blades a maximum angle of 180° is possible. The enclosed angle between the lateral blades limits the maximum opening width of the valve blade. This valve opens and closes the entire profile of the valve ring, without grid structure (22) and without radial ribs. The slanted chamfers (3 and 4) at the sides of the main area (2) of the valve blades and at the upper edge of the lateral blades (13) create a closing force directed radially to the valve axis (A), only generated by the backflow of the medium. For this reason, the valve is able to work autonomously and reliably in any position. A valve ring with very thin ribs according to FIG. 7*j*, 7*k* or 7*l* considerably increases the safety of the valve for applications in human bodies.

FIG. 9 presents two views of a second valve (V2) according to the invention, a) in opened, b) in closed state, with the lateral blades being reduced to a minimum. The narrow segments (15R and 15L) of the lateral blades feature one flat surface each, placed on top of each other and located behind the valve blades (1), when the valve is closed. They are used to synchronize the movement of the valve blades and to limit their opening. Their three rotary axes intersect with the rotary axes (9) of the valve blades at the valve ring (21*c*) in a particular point, in which the lower corners of the valve blades contact the valve ring.

FIG. 10 shows two views of a third valve (V3) according to the invention, a) in opened, b) in closed state. For this type of valve, the valve blades according to FIG. 3 are used with edges (16 and 17) at both sides, at least partially designed as lock elements. The elements of the swivel joints (11) at the edges (9) of the valve blades and at the edges of the valve ring may be manufactured as film joint or as fiber joint, or—as shown here—directly at the parts themselves. The cutouts show a negative (16) and a positive (17) element of the lock each a) in opened and b) in closed state of the valve blades. The valve ring (21c) corresponds to valve ring (21b) without ribs.

FIG. 11 shows two views of a fourth valve (V4) according to the invention, a) in opened, b) in closed state. For this type of valve, the valve blades according to FIG. 4 are used with wedge-shaped elements edges (8 and 19) at both sides. The positive wedge-shaped edge (8) of each valve blade, in retracted state of the valve, together with the negative wedge-shaped edge (7b) of the right adjacent valve blade forms a knife-edge-, respectively wedge-joint, also in some countries called prismatic joint. The elements of the joints (11) at the edges (9) of the valve blades and at the edges of the valve ring may be manufactured as film joint or as fiber joint, or—as shown here—directly at the parts themselves. The cutouts show the right edge (8) rotating from opened to closed state of the valve, inside the V-shaped slot (19) of the left edge of valve blade (1e), around the tip (7b and 8) of both wedges. A small axial degree of freedom may preferably be provided for the swiveling joint (11) of the valve blade with the valve ring, enabling the wedges to be pressed against each other, when the valve is in closed state. The valve ring (21c) corresponds to valve ring (21b) without ribs.

FIG. 12 shows an example of the assembly procedure for a valve with valve blades. The blades are connected by a fabric mutually and to the valve ring (21a) in swiveling configuration. First the fiber fabric joints (12a) are mounted to the valve ring (21a). Then the tube-shaped envelope (24) with the comprised hexagonal step (25) is glued or pressed in on the valve ring (21a) in correct position.

A great variety of models for the blade type check valve covered by this invention is provided, by combining different shapes of valve blades with appropriate joints and housings, with or without grid structure or protective envelope.

All versions of the check valve (V1 to V5) may preferably be produced by three-dimensional printing in one single piece, consisting of plastic or a mixture of plastic and metal powder.

The features detailed in this description, in drawings and claims, may be relevant for the realization of the invention, whether individually or in any combination. Particularly the combination of features from different examples may be advantageous to create further design versions according to the invention.

REFERENCE DESIGNATIONS

1: Different versions of the valve blade.
2: Main area of the valve blade, oriented to the inside of the valve, respectively to the valve axis.
3: Left slanted lateral face of the valve blade.
4: Right slanted lateral face of the valve blade.
5: Lateral face of the valve blade oriented towards the valve ring.
6: Rear side of the valve blade, oriented towards the outside.
7: Left side respectively edge of the main area.
8: Right side respectively edge of the main area.
9: Edge of the main area oriented towards the valve ring.
10: Burls located on the main area.
11: Elements of a swivel joint.
12: Joint made of plastic in the form of a film joint or consisting of a fabric of biological or synthetic fibers.
13: Lateral blade.
14: Joint elements of lateral blades.
15: Segments of lateral blades.
16: Edge of the valve blade, designed as a hollow body or as a negatively shaped edge.
17: Positively shaped edge of the valve blade (full edge).
18: Bores at the outside of the open hollow body.
19: Wedge-shaped slot in a conical or pyramidal envelope.
20: The conical or pyramidal envelope of a wedge-shaped hollow slot.
21: A valve ring with a hexagonal though bore.
22: Radial rib structure with and without honeycomb formation.
23: Saw-tooth shaped recesses in the diagonal ribs.
24: Tube-shaped protective envelope (housing) of the valve.
25: Angular, particularly hexagonal step inside the protective envelope of the valve.
A: Center axis of valve and valve housing.
A7: Axis of the hollow cylindrically expanded body around edge 7b.
A8: Axis of the full cylindrically expanded body around edge 8b.
A9: Rotary axis of joint element 11a and 11b.
n: Number of faces of the angular bore of the valve ring=number of valve blades.

The invention claimed is:

1. An automatically working blade-type check valve, operated without external energy supply, opened and closed by the current of a gaseous or liquid medium, comprising n (at least three) triangular-shaped or triangular valve blades, the valve blades being thicker-walled in a middle area and thinner-walled toward all edges and tips of the valve blades, essentially grouped in circular configuration around a polygonal (n corners) through hole or bore of a valve ring, at one side accommodated by at least one hinge element each, each of the valve blades being integral with the at least one hinge element.

2. A blade-type check valve according to claim 1, further comprising elastic preloading elements between the valve blades, intended for synchronization of the movement of the valve blades.

3. A blade-type check valve according to claim 2, wherein the valve blades, the valve ring, and the elastic preloading elements are manufactured together as one piece.

4. A blade-type check valve according to claim 1, further comprising an open pyramidal grid structure at the valve ring, acting as a support and improved seal of the valve blades, the opening of the valve blades being limited by leaning bulge-shaped ribs at a rear side of the valve blades on a case.

5. A blade-type check valve according to claim 1, wherein the valve ring is placed in, or is a part of, a cylindrical and tubular case.

6. A blade-type check valve according to claim 5, wherein the opening of the valve blades is limited by leaning bulge-shaped reinforcement material projection at a rear side of the valve blades on an inner wall of the case.

7. A blade-type check valve according to claim 6, wherein the valve blades and the valve ring are manufactured together as one piece.

8. A blade-type check valve according to claim 1, further comprising elastic preloading elements between the valve blades and the valve ring, intended for closing the valve blades.

9. A blade-type check valve according to claim 8, wherein the valve blades, the valve ring, and the elastic preloading elements are manufactured together as one piece.

10. An automatically working blade-type check valve, operated without external energy supply, opened and closed by the current of a gaseous or liquid medium, comprising n (at least three) triangular-shaped or triangular valve blades, essentially grouped in circular configuration around a polygonal (n corners) through hole or bore of a valve ring, at one side accommodated by at least one hinge each, wherein each valve blade requires one right lateral blade and one left lateral blade, each right lateral blade and each left lateral blade being connected by a joint to a respective valve blade in a swiveling configuration, and each of the right lateral blades of a valve blade is connected to the left lateral blade of the right adjacent valve blade, essentially in a swiveling manner.

11. A blade-type check valve according to claim 10, wherein the mutually connected right and left lateral blades of adjacent valve blades form a joint disposing of a swiveling angle limited to 180°, such that during closure of the valve, the lateral blades radially move towards outside, from the center axis in star shaped orientation, being placed over each other behind the main blades in a folded manner.

12. A blade-type check valve according to claim 11, wherein the joints between the valve blades and the lateral blades and the joints between the lateral blades are provided only partially, and/or only to a certain quantity.

13. A blade-type check valve, operated without external energy supply, opened and closed by the current of a gaseous or liquid medium, comprising n (at least three) triangular-shaped or triangular valve blades, essentially grouped in circular configuration around a polygonal (n corners) through hole or bore of a valve ring, at one side accommodated by at least one hinge element each, wherein edges on both a right side and a left side of each of the valve blades are at least partially designed as complementary parts such that one of the edges of each of the valve blades inserts into another of the edges of an adjacent one of the valve blades during closure of the blade-type check valves.

* * * * *